US010780051B2

(12) United States Patent
Wilner et al.

(10) Patent No.: US 10,780,051 B2
(45) Date of Patent: Sep. 22, 2020

(54) PROGRAMMED CARGO RELEASE USING NUCLEIC ACID-STABILIZED MICELLES

(71) Applicant: Albert Einstein College of Medicine, Bronx, NY (US)

(72) Inventors: Samantha E. Wilner, Bronx, NY (US); Matthew Levy, New Rochelle, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/510,285

(22) PCT Filed: Oct. 7, 2015

(86) PCT No.: PCT/US2015/054365
§ 371 (c)(1),
(2) Date: Mar. 10, 2017

(87) PCT Pub. No.: WO2016/057597
PCT Pub. Date: Apr. 14, 2016

(65) Prior Publication Data
US 2017/0304200 A1    Oct. 26, 2017

Related U.S. Application Data

(60) Provisional application No. 62/061,772, filed on Oct. 9, 2014.

(51) Int. Cl.
| | | |
|---|---|---|
| *C12N 15/11* | (2006.01) | |
| *A61K 9/107* | (2006.01) | |
| *A61K 47/69* | (2017.01) | |
| *A61K 47/26* | (2006.01) | |

(52) U.S. Cl.
CPC .............. *A61K 9/107* (2013.01); *A61K 47/26* (2013.01); *A61K 47/6907* (2017.08); *A61K 9/1075* (2013.01)

(58) Field of Classification Search
None
See application file for complete search history.

(56) References Cited

U.S. PATENT DOCUMENTS

| | | | | |
|---|---|---|---|---|
| 6,441,158 B1 * | 8/2002 | Dynan | ............... | C12N 15/1137 536/23.1 |
| 2002/0031775 A1 | 3/2002 | Erikson et al. | | |
| 2003/0113716 A1 | 6/2003 | Erikson et al. | | |
| 2003/0119768 A1 | 6/2003 | Madden et al. | | |
| 2011/0218334 A1 | 9/2011 | Maier et al. | | |
| 2012/0065125 A1 | 3/2012 | Yu et al. | | |
| 2012/0177723 A1 * | 7/2012 | Torchilin | ............... | C12N 15/111 424/450 |

OTHER PUBLICATIONS

Selden et al, Chemically Programmed Cell Adhesion with Membrane-Anchored Oligonucleotides, JACS, 2012,134: 765-768 and supplemental information, pp. S1-S13 (Year: 2012).*
Bates et al, Discovery and development of the G-rich oligonucleotide AS1411 as a novel treatment for cancer, 2009, Experimental and Molecular Pathology, 86: 151-164 (Year: 2009).*
Petraccone et al, Energetic Aspects of Locked Nucleic Acids Quadruplex Association and Dissociation, Biopolymers,2006, vol. 83, 584-594 (Year: 2006).*
Cheng et al, Enhanced Hepatic Uptake and Bioactivity of Type 1(I) Collagen Gene Promoter-Specific Triplex-Forming Oligonucleotides after Conjugation with Cholesterol, the Journal of Pharmacology and Experimental Therapeutics, 2006, vol. 317, 2: 797-805 (Year: 2006).*
Dentinger et al, DNA-Mediated Delivery of Lipophilic Molecules via Hybridization to DNA-Based Vesicular Aggregates, Langmuir, 2006, 22: 2935-2937 (Year: 2006).*
Edwardson et al, Site-specific positioning of dendritic alkyl chains on DNA cages enables their geometry-dependent self-assembly, Nature Chemistry, published online in Sep. 2013, vol. 5, pp. 868-875 (Year: 2013).*
Hatefi et al, Camptothecin Delivery Methods, Pharmaceutical Research, 2002, vol. 19, No. 10: 1389-1399 (Year: 2002).*
PCT International Search Report and Written Opinion dated Dec. 31, 2015 for PCT International Patent Application No. PCT/US2015/054365, 10 pages.
Musacchio T et al., entitled "Effective Stabilization and Delivery of siRNA: Reversible siRNA-Phospholipid Conjugate in Nanosized Mixed Polymeric Micelles," Bioconjug Chem, Aug. 18, 2010, vol. 21, No. 8, pp. 1530-1536.
Waybrant B et al., entitled Effect of Polyethylene Glycol, Alkyl, and Oligonucleotide Spacers on the Binding, Secondary Structure, and Self-Assembly of Fractalkine Binding FKN-S2 Aptamer-Amphiphiles, Langmuir, Jun. 17, 2014, vol. 30, No. 25, pp. 7465-7474.

* cited by examiner

*Primary Examiner* — Ekaterina Poliakova-Georgantas
(74) *Attorney, Agent, or Firm* — Fox Rothschild LLP

(57) ABSTRACT

Methods and compositions for serum-stabilizing micelles for drug delivery or imaging agent delivery are provided, as well as methods and compositions to enhance micelle-mediated drug delivery. This invention provides a process for synthesizing a lipid micelle comprising one or more lipid-oligonucleotide conjugate molecules, the process comprising contacting an amount of lipid molecules with an amount of lipid-oligonucleotide conjugate molecules sufficient to create a lipid micelle comprising lipid-oligonucleotide conjugate molecules.

16 Claims, 13 Drawing Sheets

PROGRAMMED CARGO RELEASE USING NUCLEIC ACID-STABILIZED MICELLES

CROSS-REFERENCE TO RELATED APPLICATIONS

This application is a U.S. national stage entry under 35 U.S.C. § 371 of PCT International Patent Application No. PCT/US2015/054365, filed on Oct. 7, 2015, which claims the benefit of U.S. Provisional Patent Application No. 62/061,772, filed on Oct. 9, 2014, the contents of each of which are incorporated herein by reference into the subject application.

BACKGROUND OF THE INVENTION

Throughout this application various publications are referred to in square brackets. Full citations for these references may be found at the end of the specification. The disclosures of these publications, and all patents, patent application publications and books referred to herein, are hereby incorporated by reference in their entirety into the subject application to more fully describe the art to which the subject invention pertains.

Lipid micelles generated by the self-assembly of monomers represent an important class of nanoparticle with the potential to enhance the solubility and delivery of hydrophobic drugs. Their small size (<20 nm) makes them ideal candidates for both passive tumor uptake and deep tissue penetration. However, as with all micelles, formation is a dynamic process in which lipid monomers exist in equilibrium with micelles. Micelle formation occurs when lipid monomers reach the critical micelle concentration (CMC; FIG. 1A). For in vivo applications, micelles with low CMC values are typically preferable as systemic injection results in significant dilution favoring the monomeric state. However, the in vivo stability of micelles is further affected by the presence of serum proteins such as BSA, which can interact with hydrophobic lipid tails skewing the equilibrium. Thus, even at concentrations higher than the critical micelle concentration, when exposed to serum proteins, the equilibrium shifts to the monomeric state, releasing any encapsulated components before these particles can reach their target (FIG. 1A).

A variety of approaches have been employed to stabilize micelles ranging from chemically crosslinking their hydrophobic tails [1] to linking the hydrophilic head groups through covalent [2,3] and sometimes reversible (reducible) linkages. Recently, work from Xu and colleagues demonstrated that by engineering lipid head groups composed of heavily PEGgylated peptides designed to form a 3-helix bundle, they could generate ~15 nm micelles which remained stable due to the intermolecular head group interactions even in the presence of serum proteins (50 mg/mL BSA) for >12 hr at 37° C. [4,5].

The present invention addresses the need for alternative approaches to stabilize micelles for drug-delivery and to enhance micelle-mediated drug delivery.

SUMMARY OF THE INVENTION

This invention provides a process for synthesizing a lipid micelle comprising one or more lipid-oligonucleotide conjugate molecules, the process comprising contacting an amount of lipid molecules with an amount of lipid-oligonucleotide conjugate molecules sufficient to create a lipid micelle comprising lipid-oligonucleotide conjugate molecules.

This invention also provides a lipid micelle comprising one or more lipid-oligonucleotide conjugate molecules, the lipid micelle made by the process described herein.

This invention also provides a composition comprising a lipid micelle comprising one or more lipid-oligonucleotide conjugate molecules, wherein the micelle contains a predetermined drug or imaging molecule, and wherein a first portion of the oligonucleotide of the lipid-oligonucleotide conjugate molecules is capable of forming parallel G-quadruplex with other oligonucleotides of the same sequence.

This invention also provides a method of delivering a drug to a target in a subject, comprising administering to the subject an amount of the composition described herein, wherein the predetermined drug is the drug to be delivered to the target, and wherein the subject is also subsequently administered an amount of an antisense oligonucleotide fully complementary to the second portion of the oligoribonucleotide sufficient to disrupt the micelle and deliver the drug to a target.

This invention also provides a method of delivering a drug to a target in a subject, comprising administering to the subject an amount of the composition of any of the composition described herein, wherein the predetermined drug is the drug to be delivered to the target, in an amount sufficient to deliver the drug to the target.

This invention also provides a method of increasing the efficacy of a micelle-delivered drug to a target in a subject, comprising administering to a subject the drug as the predetermined drug of the composition described herein, in an amount sufficient to deliver the drug to the target with increased efficacy as compared to via a micelle not comprising one or more lipid-oligonucleotide conjugate molecules, wherein a first portion of the oligonucleotide of the lipid-oligonucleotide conjugate molecules is capable of forming parallel G-quadruplex with other oligonucleotides of the same sequence.

DETAILED DESCRIPTION OF THE INVENTION

Figure 1A:
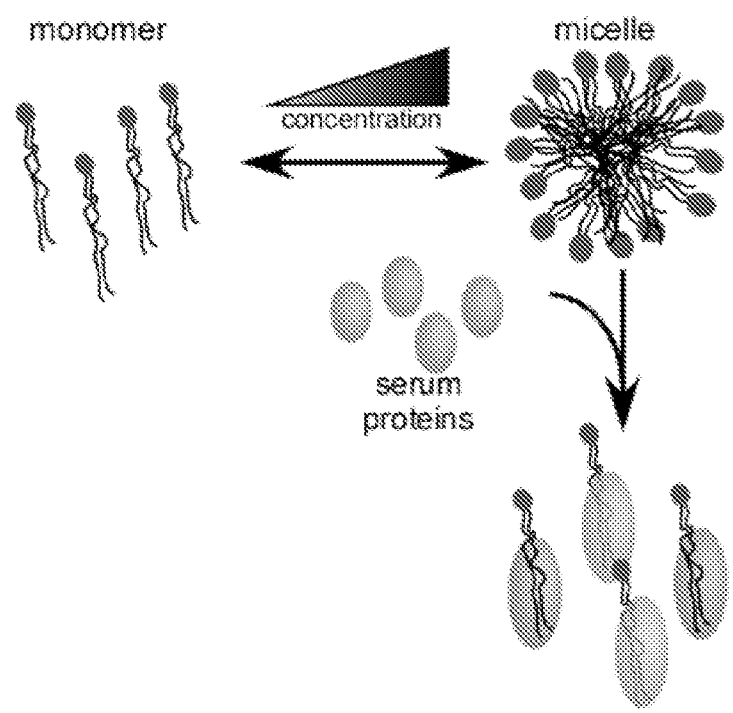
FIG. 1A-1B. Micelle schematic. (A) Micelle stability is concentration and environment dependent. Lipid monomers (1) form micelles above a critical micelle concentration, but this particle formation is disrupted by interactions with serum proteins and dilution in vivo. (B) Intermolecular interactions between L-UGGGU headgroups result in g-quadruplex formation.

Herein is described methods and compositions regarding nucleic acid-stabilized micelles and their use in targeted and/or enhanced drug delivery, including serum-stabilization.

This invention provides a process for synthesizing a lipid micelle comprising one or more lipid-oligonucleotide conjugate molecules, the process comprising contacting an amount of lipid molecules with an amount of lipid-oligonucleotide conjugate molecules sufficient to create a lipid micelle comprising lipid-oligonucleotide conjugate molecules.

In an embodiment, the oligonucleotide of the lipid-oligonucleotide conjugate is an oligoribonucleotide. In an embodiment, the oligonucleotide of the lipid-oligonucleotide conjugate is an oligodeoxynucleotide.

In an embodiment, the oligoribonucleotide is 2 to 60 ribonucleotides in length. In other embodiments, the oligoribonucleotide is 3 to 30 ribonucleotides in length, or 2 to 6 nucleotides in length.

In an embodiment, the oligonucleotide comprises one or more 2'OMe-, 2'F-, 2'NH$_3$-, or 2'H-modified residue and/or phosphophosphorothioate. In an embodiment, all the residues of the oligonucleotide are 2'OMe-, 2'F-, 2'NH$_3$-, or 2'H-modified residues or comprise phosphophosphorothioate.

In an embodiment, the oligonucleotide is attached at its 5' end to a lipid molecule of the lipid-oligonucleotide conjugate molecule. In an embodiment, the oligonucleotide is attached at its 3' end to a lipid molecule of the lipid-oligonucleotide conjugate molecule. In an embodiment, there is a mix of oligo-lipid conjugates where some oligonucleotides are attached at the 5' end to a lipid and other oligonucleotides are attached at the 3' end to a lipid.

In an embodiment, a first portion of the oligonucleotide is capable of forming parallel G-quadruplex with other oligonucleotides of the same sequence. In an embodiment, a second portion of the oligonucleotide is not capable of forming parallel G-quadruplex with other oligonucleotides of the same sequence. In an embodiment, a second portion of the oligonucleotide has a different sequence to the first portion. In an embodiment, a second portion of the oligoribonucleotide has a fully complementary antisense partner oligonucleotide hybridized thereto. In an embodiment, a second portion of the oligoribonucleotide is capable of binding to a receptor protein when in the presence of the receptor protein.

In an embodiment, the micelle further comprises an additional oligonucleotide, at least a portion of which is on external surface of the micelle, and which portion binds to a receptor protein. In an embodiment, the receptor protein is present on a cell of a subject.

In an embodiment, the receptor protein is present on a tumor cell of a subject. In an embodiment, the receptor protein is preferentially expressed on tumor cells over non-tumorous cells of a subject. In an embodiment, the sequence of a first portion of the oligoribonucleotide is UGGGU.

In an embodiment, the sequence of a first portion of the oligoribonucleotide is 5' relative to the second portion of the oligoribonucleotide.

In an embodiment, the micelles can target cell surface receptors and be taken up by the cells. The targeting of cell surface receptors can be linked to a triggering mechanism that causes the micelle to blow up. In an embodiment, the micelles can target soluble proteins and these can cause the micelle to blow up. In different embodiments, the blow-up mechanism can be engineered in the micelle itself on either the oligo with the lipid or on a oligo hybridized to the lipid.

In an embodiment, the lipid of the lipid-oligonucleotide conjugate molecule comprises 1,2-dioctadecyl-sn-glycerol; a C12, C14, C16, C18, C20 or C22 lipid; an ether-, ester- or amide-linked lipid; cholesterol; or cholic acid. In an embodiment, the lipid-oligonucleotide conjugate molecule comprises 1,2-dioctadecyl-sn-glycerol phosphoramidite.

In different embodiment, the diameter of the lipid micelle is 5-60 nm or 10-30 nm.

In an embodiment, the oligonucleotide of the lipid-oligonucleotide conjugate is covalently bound to the lipid of the lipid-oligonucleotide conjugate.

In an embodiment, the process further comprises contacting the lipid micelle comprising the one or more lipid-oligonucleotide conjugate molecules with an amount of a predetermined drug molecule, or of a predetermined imaging molecule, sufficient for uptake of at least a portion of the predetermined drug molecule or imaging molecule into the lipid micelle. In an embodiment, the predetermined drug molecule is an anti-tumor drug.

This invention also provides a lipid micelle comprising one or more lipid-oligonucleotide conjugate molecules, the lipid micelle made by the process described herein.

This invention also provides a composition comprising a lipid micelle comprising one or more lipid-oligonucleotide conjugate molecules, wherein the micelle contains a predetermined drug or imaging molecule, and wherein a first portion of the oligonucleotide of the lipid-oligonucleotide conjugate molecules is capable of forming parallel G-quadruplex with other oligonucleotides of the same sequence.

In an embodiment, the oligonucleotide of the lipid-oligonucleotide conjugate is an oligoribonucleotide. In an embodiment, the oligoribonucleotide is 2 to 60 ribonucleotides in length. In other embodiments, the oligoribonucleotide is 3 to 30 ribonucleotides in length, or 2 to 6 nucleotides in length.

In an embodiment, the oligonucleotide comprises one or more 2'OMe-, 2'F-, 2'NH$_3$-, or 2'H-modified residue and/or phosphophosphorothioate. In an embodiment, all the residues of the oligonucleotide are 2'OMe-, 2'F-, 2'NH$_3$-, or 2'H-modified residues or comprise phosphophosphorothioate.

In an embodiment, the oligonucleotide is attached at its 5' end to a lipid molecule of the lipid-oligonucleotide conjugate molecule. In an embodiment, the oligonucleotide is attached at its 3' end to a lipid molecule of the lipid-oligonucleotide conjugate molecule. In an embodiment, there is a mix of oligo-lipid conjugates where some oligonucleotides are attached at the 5' end to a lipid and other oligonucleotides are attached at the 3' end to a lipid.

In an embodiment, a second portion of the oligonucleotide is not capable of forming parallel G-quadruplex with other oligonucleotides of the same sequence. In an embodiment, a second portion of the oligonucleotide has a different sequence to the first portion. In an embodiment, a second portion of the oligoribonucleotide has a fully complementary antisense partner oligonucleotide hybridized thereto.

In an embodiment, a second portion of the oligoribonucleotide is capable of binding to a receptor protein when in the presence of the receptor protein.

In an embodiment, the micelle further comprises an additional oligonucleotide, at least a portion of which is on external surface of the micelle, and which portion binds to a receptor protein.

In an embodiment, the receptor protein is present on a cell of a subject. In an embodiment, the receptor protein is present on a tumor cell of a subject. In an embodiment, the receptor protein is preferentially expressed on tumor cells over non-tumorous cells of a subject. In an embodiment, the sequence of a first portion of the oligoribonucleotide is UGGGU.

In an embodiment, the sequence of a first portion of the oligoribonucleotide is 5' relative to the second portion of the oligoribonucleotide.

In an embodiment, the lipid of the lipid-oligonucleotide conjugate molecule comprises 1,2-dioctadecyl-sn-glycerol; a C12, C14, C16, C18, C20 or C22 lipid; an ether-, ester- or amide-linked lipid; cholesterol; or cholic acid. In an embodiment, the lipid-oligonucleotide conjugate molecule comprises 1,2-dioctadecyl-sn-glycerol phosphoramidite.

In an embodiment, the diameter of the lipid micelle is 5-60 nm or 10-30 nm.

In an embodiment, the oligonucleotide of the lipid-oligonucleotide conjugate is covalently bound to the lipid of the lipid-oligonucleotide conjugate. In an embodiment, the predetermined drug molecule is an anti-tumor drug.

In different embodiments, the micelles comprise siRNA, miRNA, a splice switching oligo, an immunomodulatory oligonucleotide and/or other regulatory RNA. The RNA or oligo can be appended to the exterior of the micelle.

In an embodiment, the composition further comprises a pharmaceutically-acceptable carrier.

This invention also provides a method of delivering a drug to a target in a subject, comprising administering to the subject an amount of the composition described herein, wherein the predetermined drug is the drug to be delivered to the target, and wherein the subject is also subsequently administered an amount of an antisense oligonucleotide fully complementary to the second portion of the oligoribonucleotide sufficient to disrupt the micelle and deliver the drug to a target. This invention also provides a method of delivering a drug to a target in a subject, comprising administering to the subject an amount of the composition of any of the composition described herein, wherein the predetermined drug is the drug to be delivered to the target, in an amount sufficient to deliver the drug to the target.

In an embodiment, the composition is administered into the bloodstream of a subject.

In an embodiment, the target is a tumor.

This invention also provides a method of increasing the efficacy of a micelle-delivered drug to a target in a subject, comprising administering to a subject the drug as the predetermined drug of the composition described herein, in an amount sufficient to deliver the drug to the target with increased efficacy as compared to via a micelle not comprising one or more lipid-oligonucleotide conjugate molecules, wherein a first portion of the oligonucleotide of the lipid-oligonucleotide conjugate molecules is capable of forming parallel G-quadruplex with other oligonucleotides of the same sequence.

In an embodiment, the increased efficacy is a lower serum level of the predetermined drug in the subject. In an embodiment, the increased efficacy is a lower dosage of drug required to effect a drug therapy parameter in the subject.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

The use of oligonucleotides and even single nucleotides as lipid head-groups for the formation of micelles has previously been reported (reviewed in [6]). Self-assembled DNA nanocages used to precisely arrange C12 alkylchains to assemble a hydrophobic core within a tetrahedral structure are known in different fields of use [7]. However, an oligonucleotide alone is unlikely to stabilize a micelle. Herein is disclosed a technique using multiple selected oligonucleotides engineered to cause interactions between head groups that was empirically determined to enhance stability.

Figure 1B:
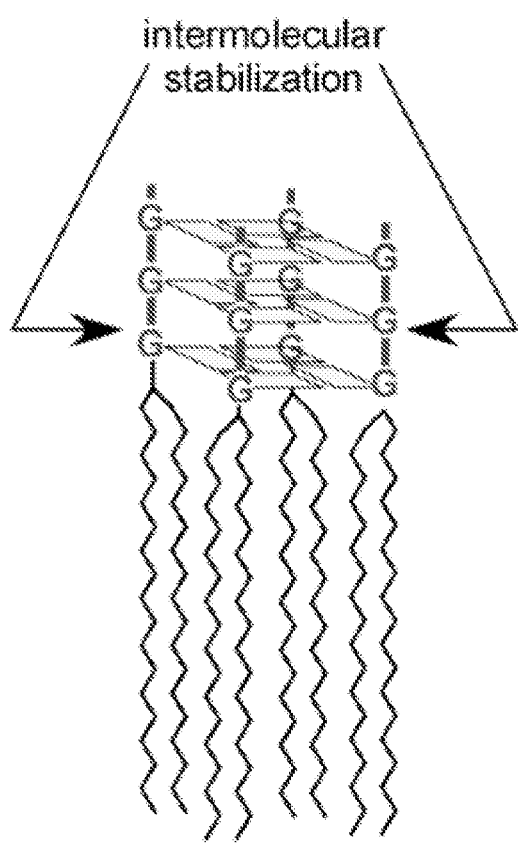
Figure 8:
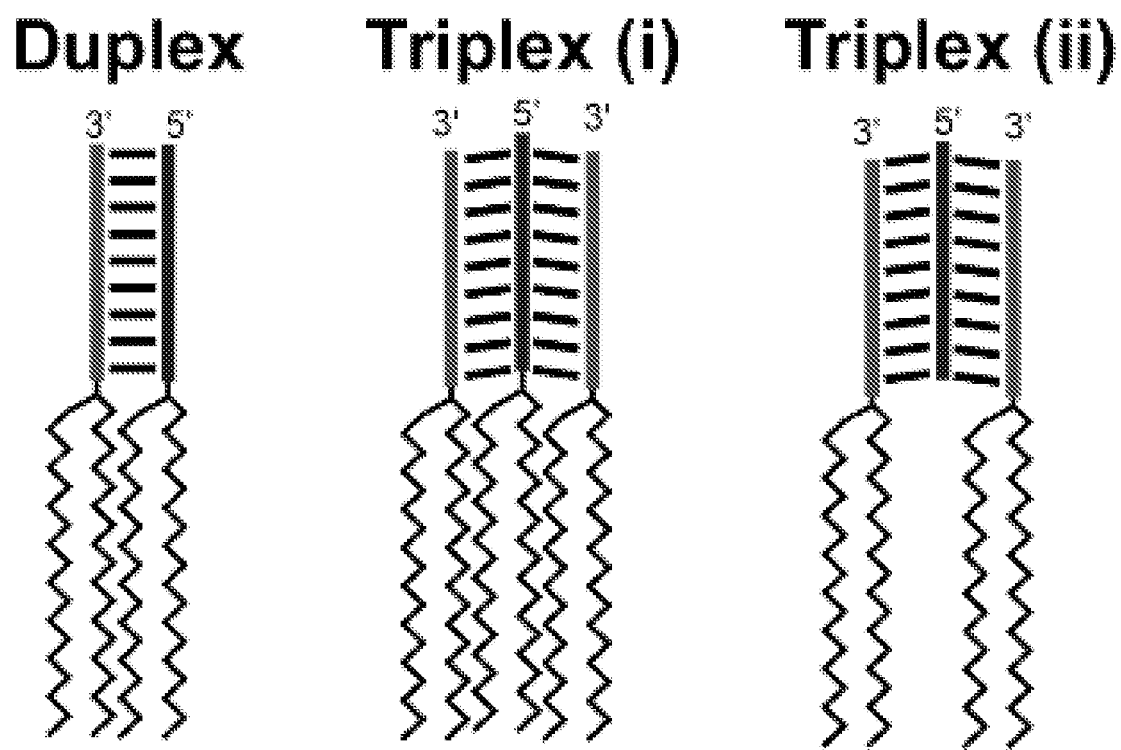
FIG. 8. Non-limiting alternative nucleic acid complexes for stabilizing micelles.

Using standard solid phase DNA/RNA synthesis and a 1,2-dioctadecyl-sn-glycerol phosphoramidite, two short oligonucleotide-lipid conjugates were synthesized composed of highly stable 2'OMe RNA bearing a 5' lipid: (1) L-UUUUU, which is predicted to not possess any intramolecular interaction and (2) L-UGGGU, which is predicted to form a parallel G-quadruplex (FIG. 1B) [8,9]. Following synthesis, deprotection, and purification, the conjugate identities were verified by LCMS and subsequently used to generate micelles. In short, the lipid conjugate, dissolved in ethanol, was dried to a film under vacuum. Following the addition of buffer (50 mM phosphate, pH 7.5 containing 5 mM KCl), the samples were heated to 65° C. for 5 minutes. The resulting clear solution was filtered through a 0.45 nm filter to remove any aggregates, and the flow through was used for subsequence experiments. It is noted that while it was initially chosen to develop OLMs with quadruplex forming head groups, other head group structures can be implemented, in particular duplexes and triplexes (FIG. 8). To generate duplexes, one can, for example, use commercially available 2'OMe RNA phosphoramidites which allow for reverse (5'→3') solid phase synthesis (Chemgenes). In the case of triplex formation, sequences known to form these structures can be employed. Two different conformations are desirable, one in which all three strands bear lipids and one in which the third strand is added in trans as a stabilizer as this provides an interesting alternative to developing micelles which can be rapidly destabilized.

Figure 2A:
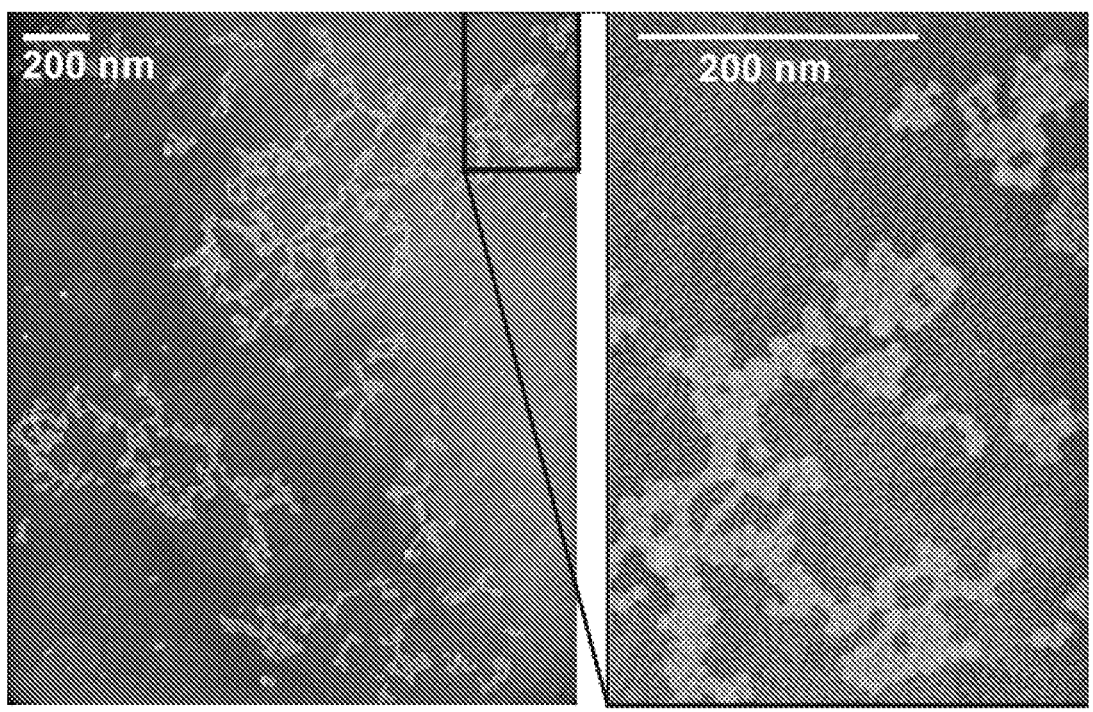
FIG. 2A-2C. Micelle characterization. (A) TEM image of L-UGGGU micelles. (B) Experimental SAXS profiles of DSPE-PEG, UGGGU, and UUUUU micelles, from top to bottom, and fitted profiles from the ellipsoid model fits. The sample concentration for each was ~2 mg/mL. For clarity, the UGGGU and UUUUU data sets were vertically offset by scaling intensity values by $10^{-2}$ and $10^{-3}$, respectively. (C) Intraparticle distance distribution p(r) for L-UUUUU micelles, L-UGGGU micelles, and DSPE-PEG micelles, each at 2 mg/mL. The p(r) of each sample is bell-shaped with DSPE-PEG and L-UGGGU micelles displaying more elongated structures. It is concluded that these micelles are nearly spherical with DSPE-PEG and L-UGGGU having slight ellipsoidal character. Peaks from top to bottom, respectively: L-UUUUU micelles, DSPE-PEG(2000) micelles and L-UGGGU micelles.
Figure 2B:
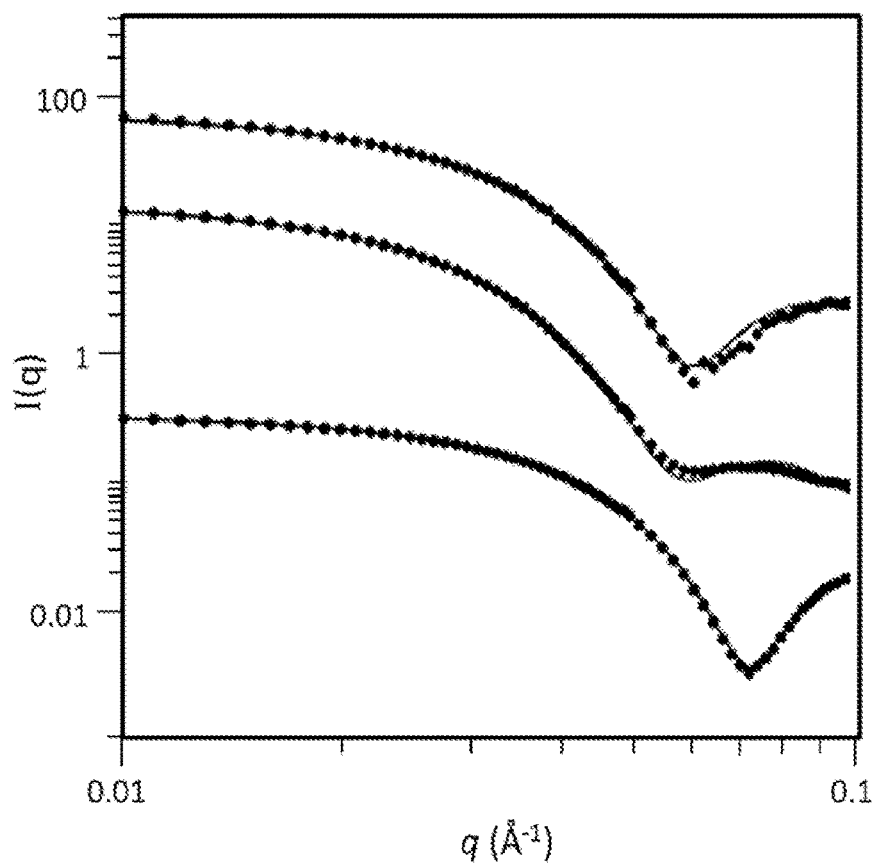
Figure 2C:
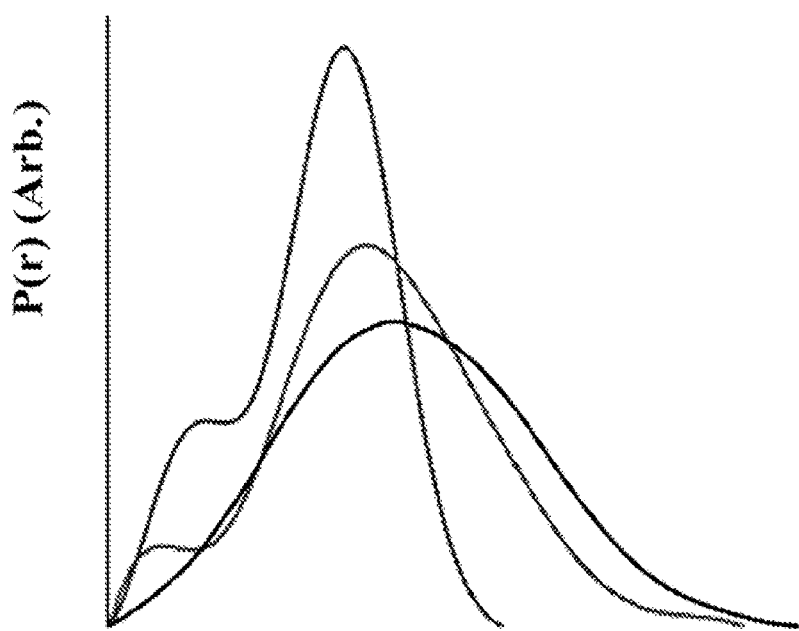

Micelles generated from L-UUUUU or L-UGGGU formed particles with diameters ~10 nm and low polydispersity (<10%), similar in size to micelles generated using the lipid amphiphile DSPE-PEG2000 as determined by dynamic light scattering. Particle size was further confirmed by negative-stain transmission electron microscopy (FIG. 2A). Based on this size and similarity to DSPE-PEG, the particles are estimated to be composed of ~90 molecules each [10]. Particle analysis by SAXS (FIGS. 2B and 2C) revealed an overall spherical nature to the particles.

Figure 3:
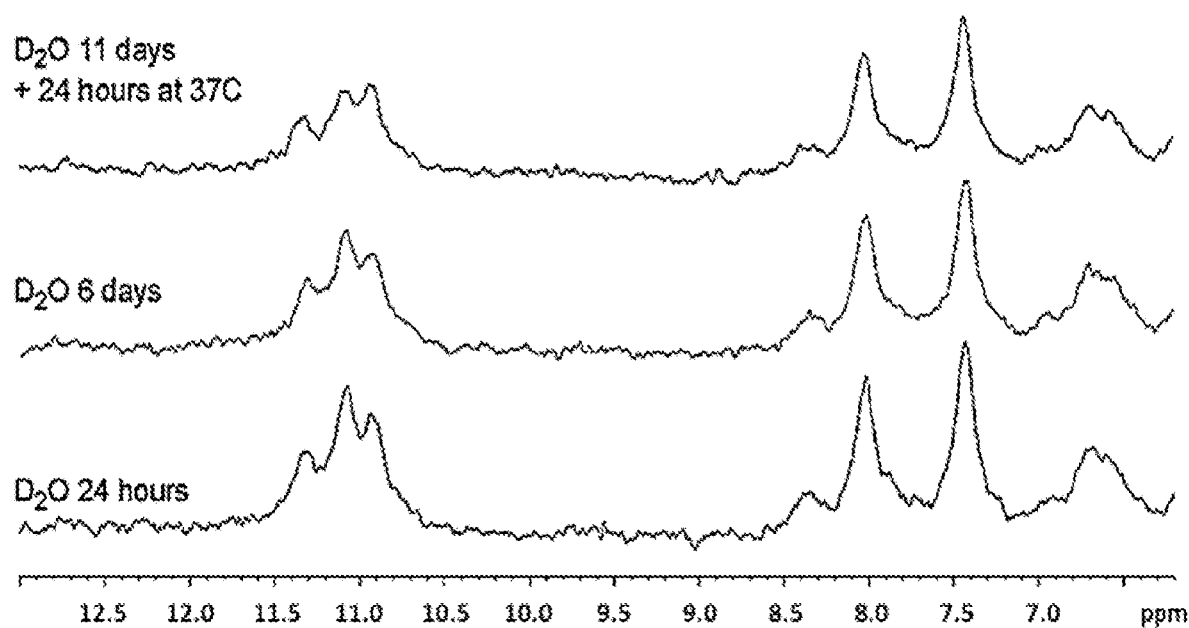
FIG. 3. Overlay of NMR spectra for L-UGGGU micelles after $D_2O$ exchange. L-UGGGU micelles were incubated in $D_2O$ for 24 hours, 6 days, and 11 days including one 24-hour incubation at 37° C. The $^1H$ NMR spectra for L-UGGGU micelles display characteristic imino proton shifts which remain resistant to deuterium exchange >24 hours.

The alteration in the shape of micelles generated with L-UUUUU versus L-UGGGU suggested that the engineered head group interactions within the UGGGU-micelles lead to an alteration in the overall micelle structure. To confirm quadruplex formation, $^1$H NMR was preformed on these micelles. Repeating guanine bases show a characteristic down field shifted imino proton at ~11 ppm that demonstrates resistance to exchange in $D_2O$ [8]. Consistent with this, the $^1$H NMR spectra for the UGGGU-micelles displayed characteristic imino protons which remained resistant to deuterium exchange >24 hours (FIG. 3). Accordingly, a similar NMR analysis of UUUUU-micelles does not show this characteristic imino proton shift (data not shown).

Figure 4A:
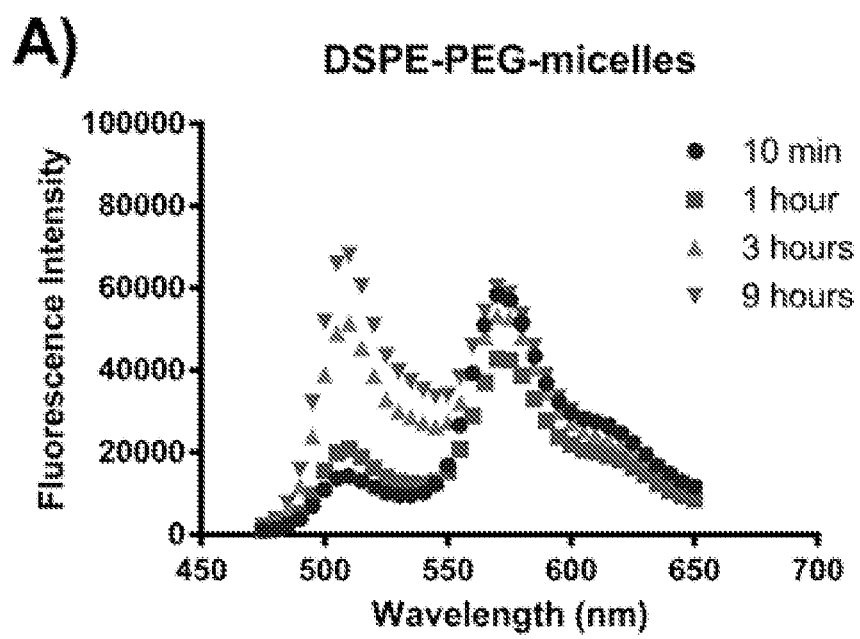
FIG. 4A-4D. FRET assay to measure micelle stability. (A) FRET spectra of DSPE-PEG2000 micelles and (B) UUUUU-micelles show an increase in fluorescence intensity at 505 nm indicating micelle destabilization. (C) FRET spectra of UGGGU-micelles. (D) Graph of normalized FRET ratio (I565/[I565+I505]) over 9 hours.
Figure 4B:
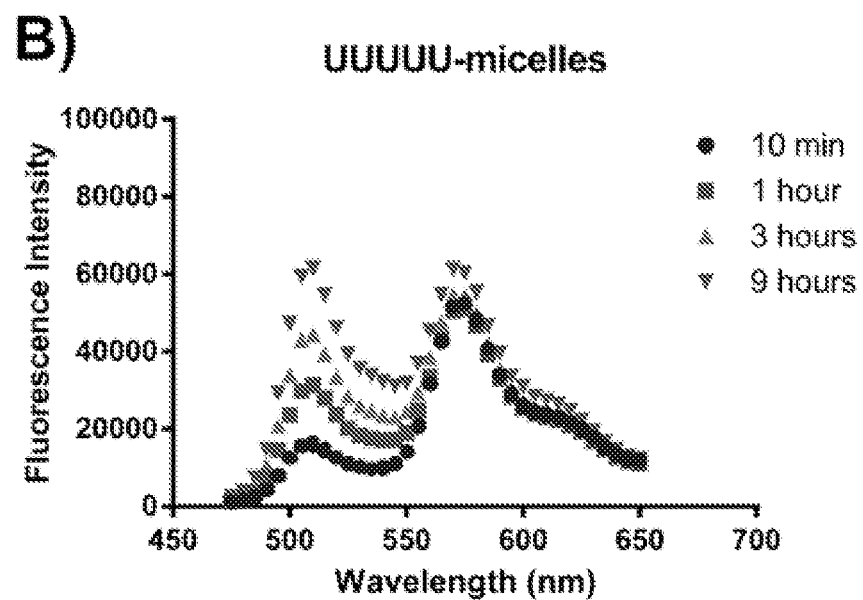
Figure 4C:
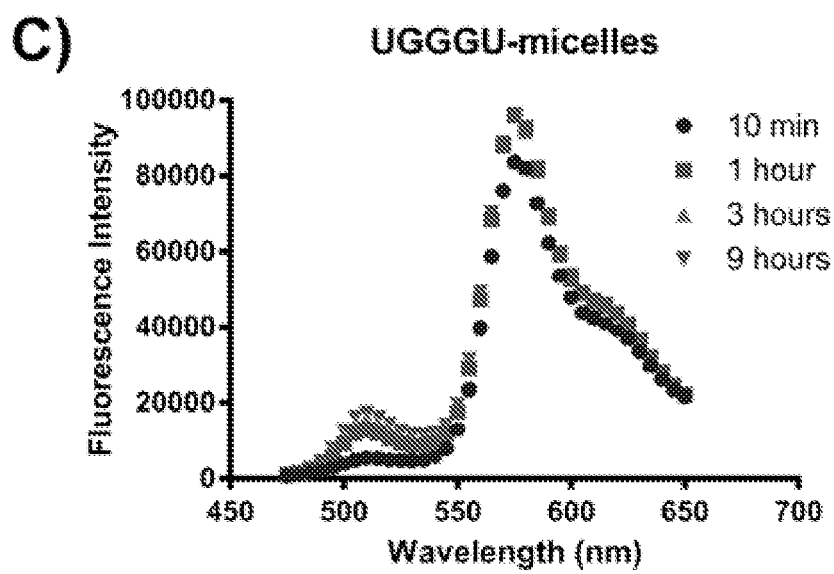
Figure 4D:
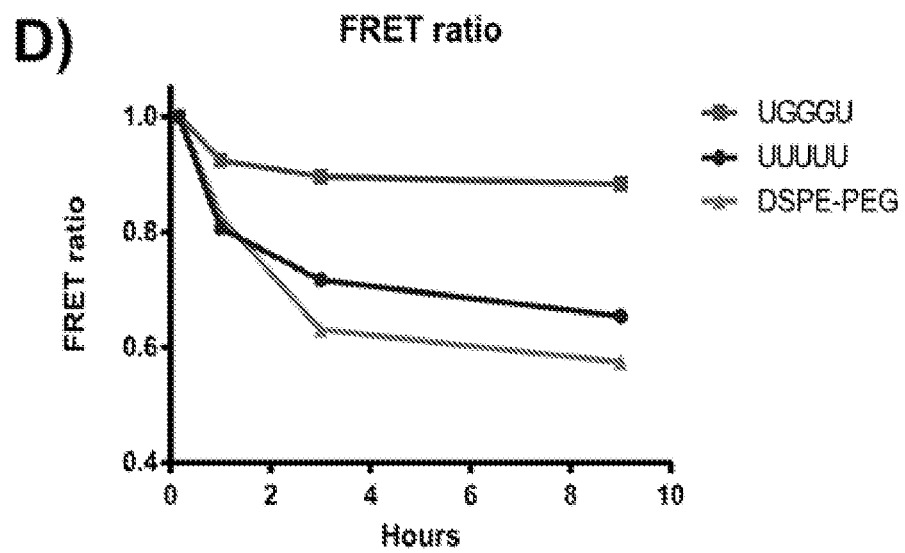

In order to assess the effects of quadruplex stabilization on micelle stability a dye release assay was utilized in which a lipophilic FRET pair (Dio/Dil) is encapsulated within the micelle and release of the dyes is monitored over time [5]. When co-encapsulated within an intact micelle, excitation at 450 nm results in FRET, and fluorescence emission is observed at 565 nm due to the close proximity of the dyes within the micelles. Release of the dyes results in their separation and an increase in fluorescence intensity at 505 nm. When both UUUUU-micelles and control micelles made of DSPE-PEG(2000) are diluted in 90% FBS, there is an increase in fluorescence intensity at 505 nm as these lipids rapidly exchange with serum proteins (FIGS. 4A and 4B). This destabilization is also marked by a decrease in the FRET ratio ($I_{565}/[I_{565}+I_{505}]$), which approaches an experimentally determined value of ~0.5 in 9 hours indicating almost complete release of encapsulated cargo (FIG. 4D). Destabilization is FBS dependent with lower concentrations of serum leading to slower release. Importantly, this change in fluorescence intensity is not observed for UGGGU-micelles. Furthermore, although the FRET ratio for UGGGU-micelles initially decreases slightly, it remains stable for >24 hours, indicating enhanced stability of the micelles and lack of exchange with serum proteins (FIGS. 4C and 4D).

Micelle stability can also be assessed by measuring the kinetics of lipid exchange [5]. To this end fluorescently labeled RNA-lipid conjugates were generated bearing a 3' fluorescein modification and used to generate micelles. Fluorescein labeled L-UUUUU and L-UGGGU lipids assembled into micelles with diameters similar to those of their unlabeled counterparts (~10 nm; data not shown). Due to the close proximity of the dyes in the headgroup, fluorescence is quenched. However, to ensure that that fluorescent quenching was due to the micelle formation and not just the formation of a quadruplexes, micelles were generated using a 5:1 ratio of unlabeled to labeled lipid conjugate. When these FITC-labeled micelles were diluted with a 600-fold excess of unlabeled micelles, the rate of fluorescence recovery was measured in the presence of buffer or serum. In the case of UGGGU-micelles, there is no increase in fluorescence in either buffer or serum, indicating that particles remain quenched over time. On the other hand, consistent with the data from dye release assays, UUUUU-micelles dequench over the course of 3 hours, suggesting exchange of fluorescently labeled lipids with unlabeled lipids.

Finally, because the CMC is an important factor in defining micelle stability especially upon dilution following systemic injection, experiments were performed to determine the CMC value for both the L-UUUUU and the L-UGGGU micelles. The standard approach using pyrene excitation yielded values consistent with literature DSPE-PEG2000 (~1 uM; [10]), but was not sensitive enough to determine the CMC value for either L-UUUUU or L-UGGGU micelles. Using lipid-oligo conjugates bearing a 3' fluorophore it was attempted to measure the CMC using fluorescence quenching as a metric for micelle formation, as has previously been reported [11, 12]. However, here again the assay was not sensitive enough and the apparent concentration required for accurate CMC determination fell below the detection limit, suggesting that CMC for both these lipid-conjugates is ≤pM (data not shown). It is interesting to note that although L-UUUUU displays a very low CMC, this value is not sufficient to maintain stability in the presence of serum proteins. Thus, a low CMC is not the only prerequisite for stability in biological fluids.

Figure 5:
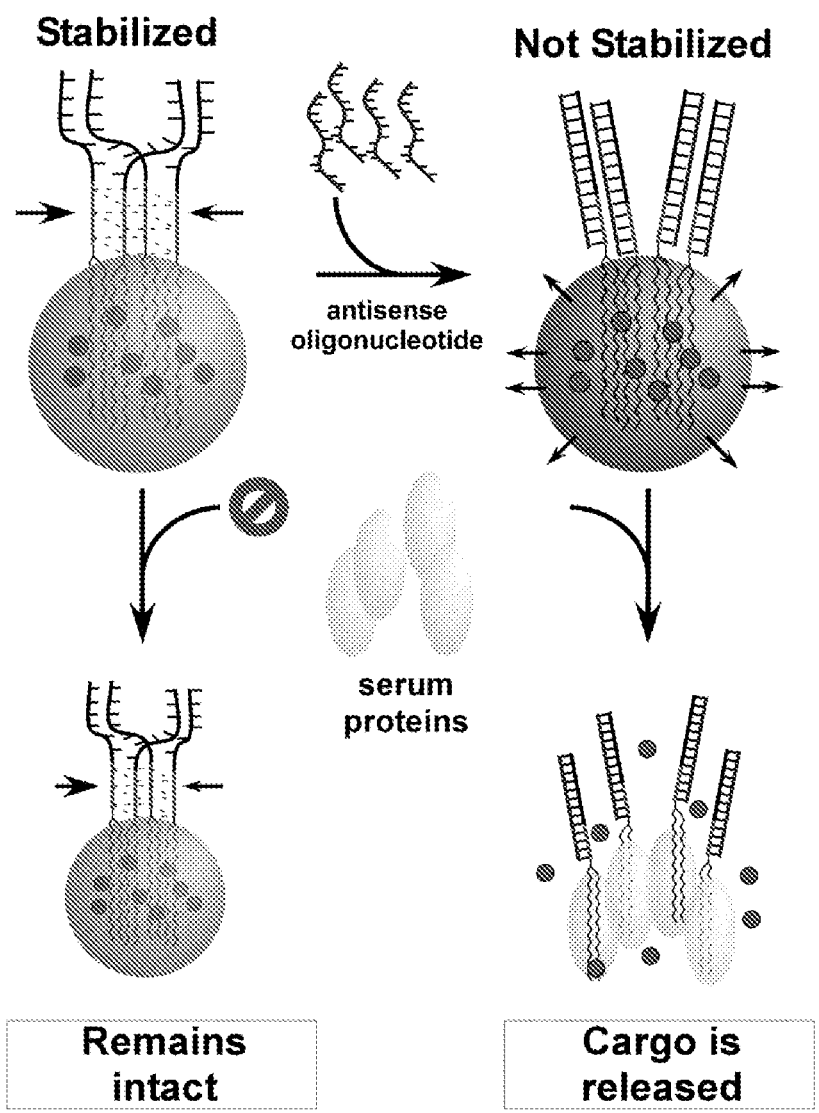
FIG. 5. Schematic of micelle destabilization using antisense oligonucleotides. UGGGU-micelles remain intact in the presence of serum proteins. Addition of antisense oligonucleotides that disrupt G-quadruplex formation results in micelle destabilization and cargo release.
Figure 6A:
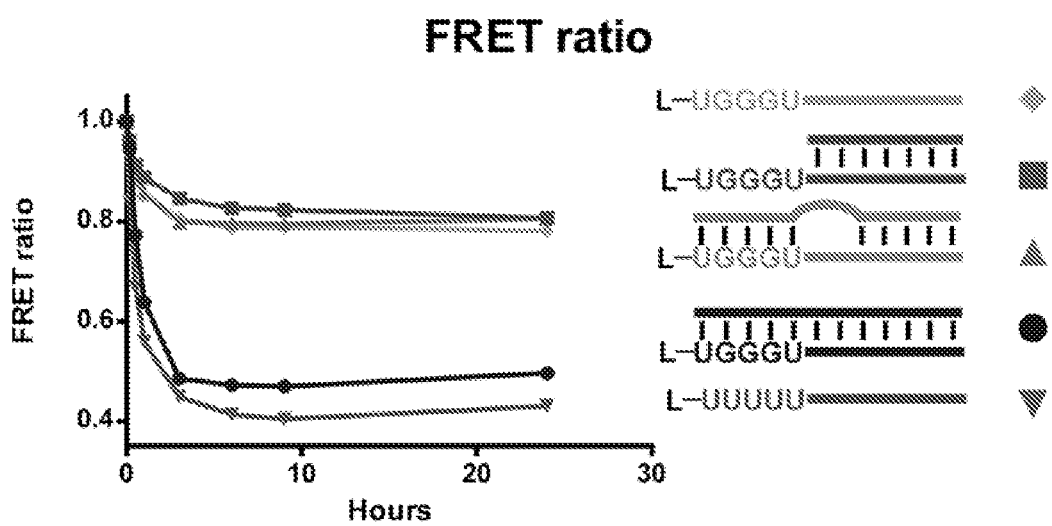
FIG. 6A-6B. Programmable micelle stability using antisense oligonucleotides. (A) Plot of FRET ratios upon addition of antisense oligonucleotides. Only the perfectly complementary oligonucleotide disrupts the stability of the UGGGU-micelles bearing a 3' extension, which looks similar to the 3' extended UUUUU-micelles. Antisense strands that do not disrupt the G-quadruplex or contain a 3-base mutation do not affect micelle stability. (B) Change in FRET ratio upon titration of the perfectly complementary antisense oligonucleotide. "Molar eq." indicates molar equivalent of antisense oligonucleotide as compared to the concentration of the extended UGGGU-micelles.

The marked difference in stability between the UUUUU-micelles and the quadruplexed UGGGU-micelles suggested that modifications at the lipid headgroup might be used to alter micelle stability and subsequently induce cargo release. To this end, UGGGU-micelles were engineered bearing a 3' oligonucleotide extension (L-UGGGU-ext) such that the addition of an antisense oligonucleotide would disrupt the stabilizing G-quadruplex (FIG. 5). Extension of the 3' end of the UGGGU sequence did not affect micelle size or stability in the presence of FBS according to the FRET stability assay (FIG. 6A). However, upon addition of equimolar amounts of a perfectly complementary oligonucleotide, micelle stability is destroyed (FIG. 6A), and the FRET ratio decreases similar to that of UUUUU-micelles with an extended 3' oligonucleotide (FIG. 6A). On the other hand, if an antisense oligonucleotide bearing a 3-base mutation is added at equimolar amounts, micelle stability is not affected (FIG. 6A). Similarly, micelles remain intact when an antisense oligonucleotide is introduced that does not hybridize with the G-quadruplex forming sequence, UGGGU (FIG. 6A). Hybridization of antisense oligonucleotides with micelles was confirmed by gel electrophoresis and by size exclusions chromatography. As with UGGGU micelles, UGGGU-ext were stable in serum for >24 hrs, but could be rapidly induced to release their cargo upon the addition of antisense oligonucleotide (FIG. 6A).

Figure 6B:
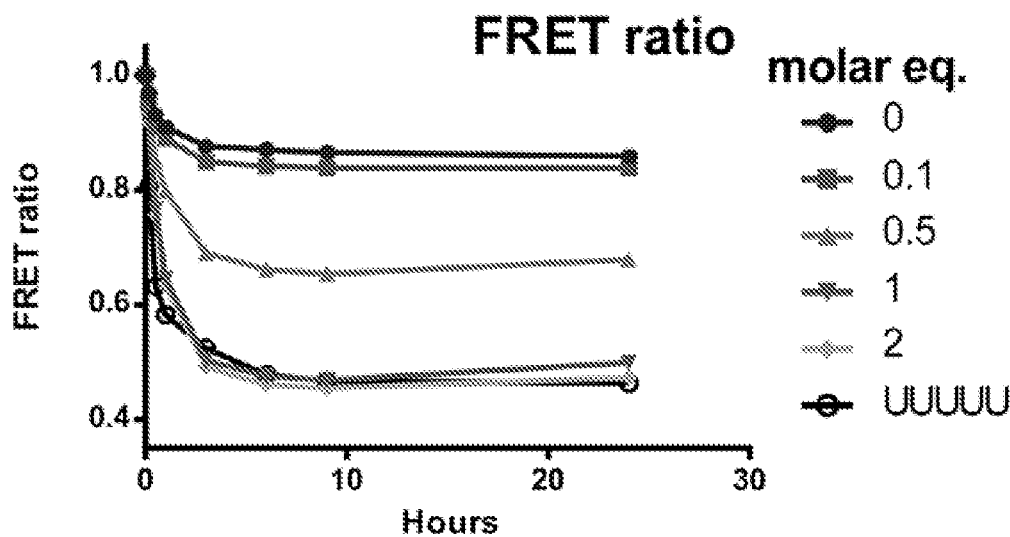
Figure 7:
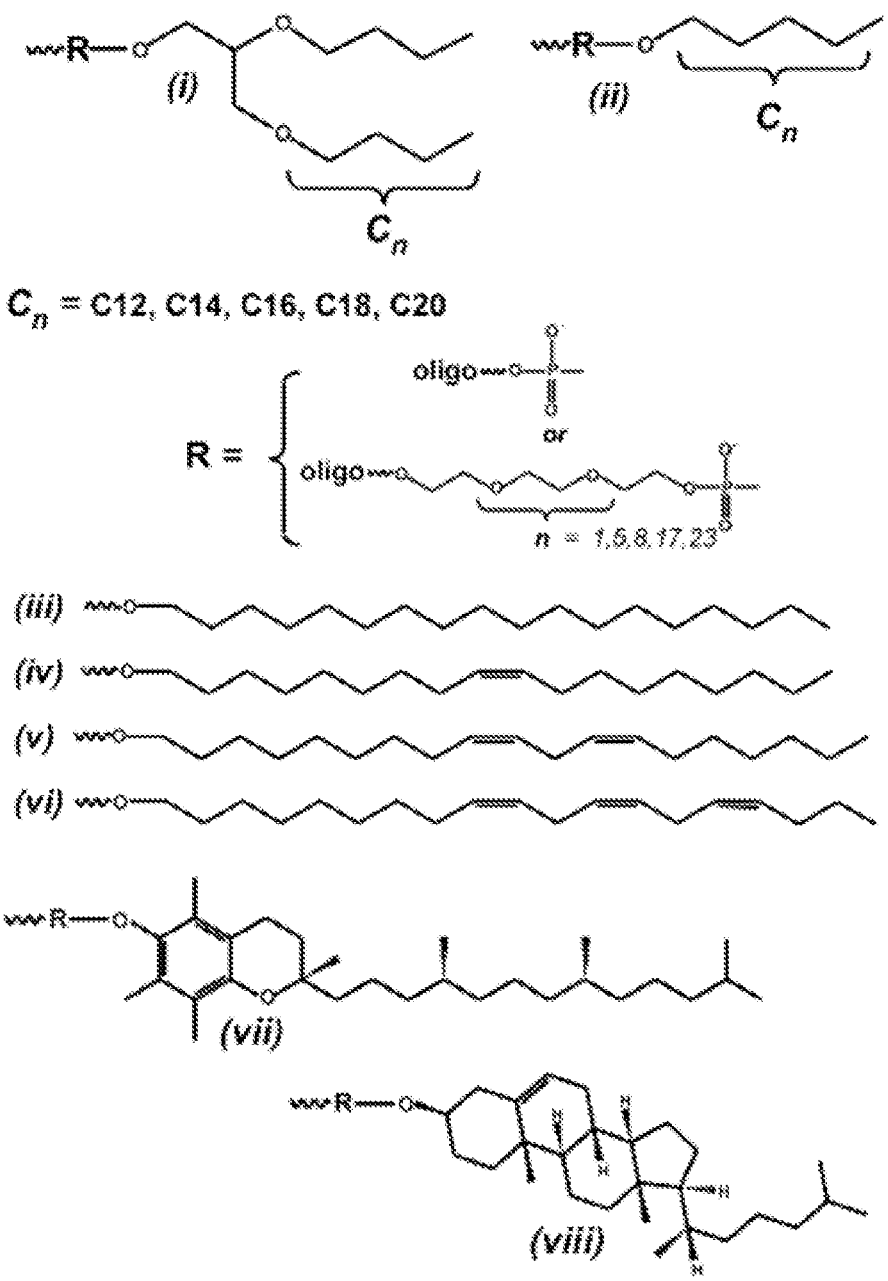
FIG. 7. Non-limiting exemplary lipids that can be used in lipid-oligonucleotide conjugates for micelles.

When experiments were performed in which molar equivalents of the perfectly complementary oligonucleotide to L-UGGGU-ext micelles were titrated in, only in the presence of equimolar (1:1) or excess (2:1) amounts of the antisense oligonucleotide is micelle stability disrupted (FIG. 6B). Interestingly, the addition of substiochiometric levels (0.5:1) resulted in intermediate levels of dye.

Targeting cells with OLMs. The ability to add oligonucleotide extensions to oligonucleotide-linked micelles (OLMs) provides a facile means to append nucleic acid based targeting ligands or aptamers. To this end, aptamer targeted OLMs were generated using an anti-transferrin receptor aptamer, and the ability of these ligands to enhance OLM uptake was assessed.

Figure 9A:
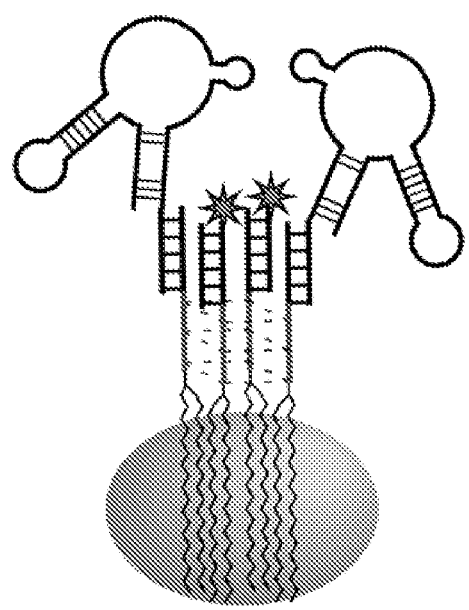
FIG. 9A-9E. Targeted uptake of OLMs into cells. OLMs labeled with dye and decorated with an anti-transferrin receptor aptamer (A) show uptake into HeLa cells by flow cytometry (B). A non-targeting control or no aptamer control do not show significant uptake. Targeted or control micelles co-encapsulating the FRET pair Dio/Dil (C) were incubated in 90% FBS overnight at 37° C. before adding to cells. Only quadruplex-forming and targeted micelles delivered cargo into cells (D), while non-targeted or non-quadruplex forming micelles (E) failed to give signal due to destabilization and loss of content in FBS.
Figure 9B:
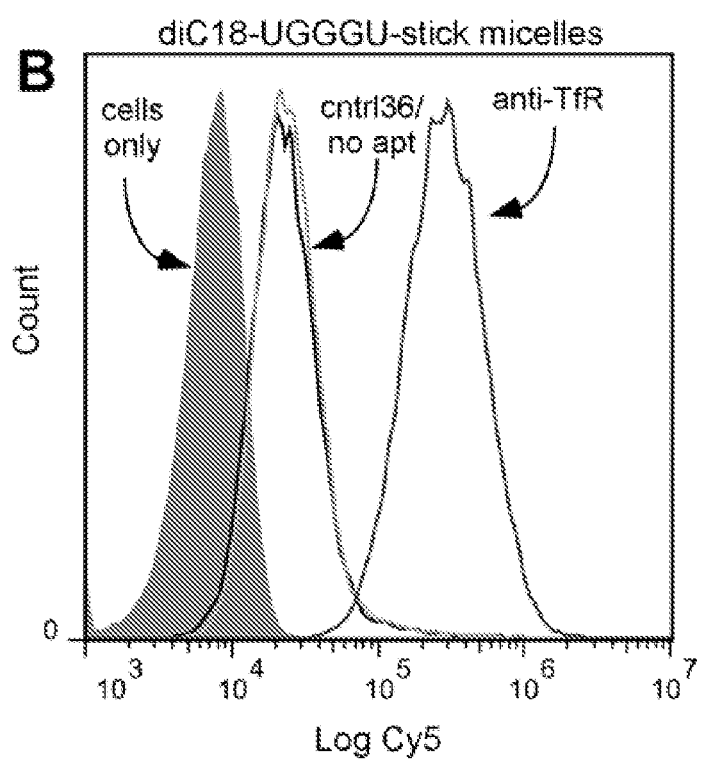

To demonstrate targeted uptake, two sets of experiments were performed. In the first, extended UGGGU micelles were generated that included an anti-hTfR aptamer, a non-targeting control aptamer (cntrl 36) or no aptamer. To monitor uptake, particles were also functionalized with a dye-labeled oligonucleotide (Dylight650) such that each particle displayed ~25 dye molecules and ~50 aptamers (FIG. 9A). Under these conditions, attachment by hybridization proceeds to ~100% as no free aptamer or labeled oligo could be detected in solution by gel electrophoresis (data not shown). It is also important to note that the aptamer and dyes are only connected via the particle and not directly connected to one another. Using these particles, cell uptake was assessed by flow cytometry using HeLa cells, a cervical cancer cell line which, like most cancers, expresses high levels of hTfR. As shown in FIG. 9B, while both the no aptamer and non-functional aptamer control particles showed some level of non-specific uptake, attachment of the anti-TfR aptamer enhanced cellular uptake by ~20-fold (FIG. 6B).

Figure 9C:
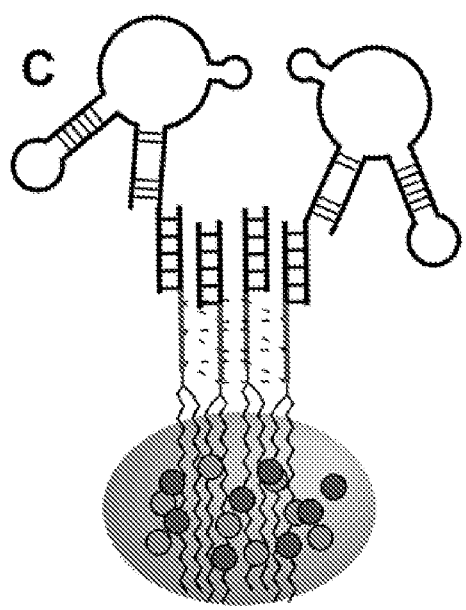
Figure 9D:
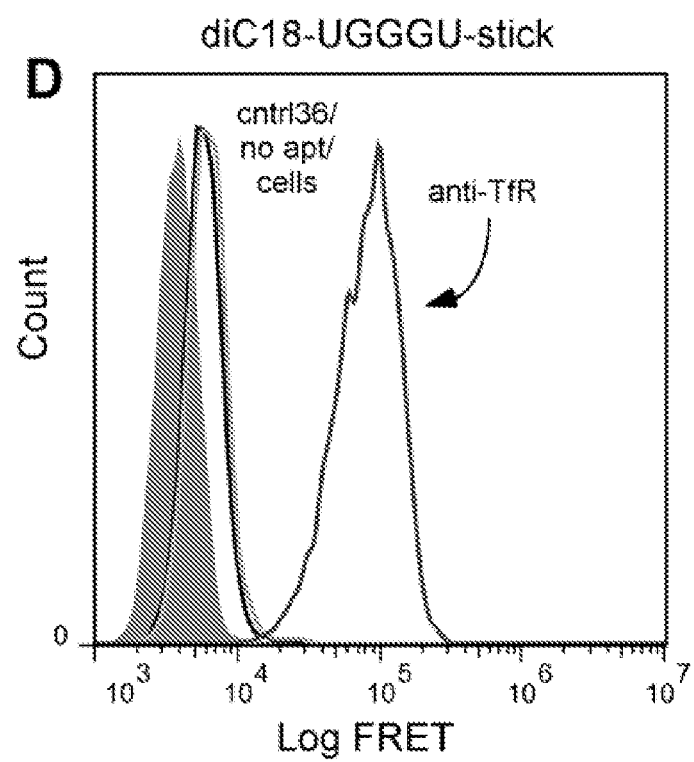
Figure 9E:
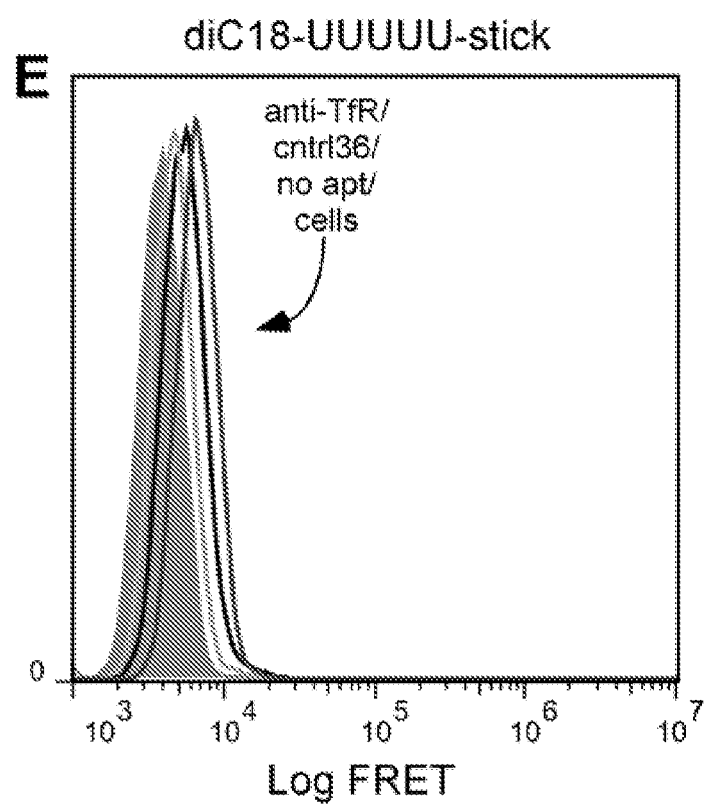

In a second set of experiments, both extended UGGGU and UUUUU micelles were generated that contained the Dio/Dil FRET pair bearing an anti-hTfR aptamer, a non-targeting control aptamer or no aptamer (FIG. 9C). To mimic in vivo conditions, the particles were pre-incubated in 90% FBS at 37° C. overnight after which they were added to HeLa cells grown in culture in 10% FBS for one hour and then analyzed by flow cytometry. As shown in FIGS. 9D and 9E which looks at the FRET signal from the encapsulated dye pair (Ex488/Em565), the targeted UGGGU micelles displayed significant levels of uptake when compared to non-targeted particles (consistent with the data in FIG. 9B). When the same experiment was performed using UUUUU particles, there is little if any uptake observed for any of the micelles, consistent with the fact that these particles are not stable in FBS and would have lost any encapsulated dye. When similar experiments were performed using micelles labeled by hybridization (as in FIG. 9A), similar results were observed, that is only the targeted UGGGU micelles, but not targeted UUUUU micelles displayed significant levels of uptake, suggesting that exposure to FBS during the overnight incubation results in more than just cargo release—the non-stabilized UUUUU micelles are actually completely falling apart and cannot be targeted (data not shown). These data demonstrate targeting of the micelles to cell surface receptors using aptamers and that after prolonged exposure to serum (24 hr), targeting only occurs using stabilized micelles.

In summary, a lipid-based micelle bearing a RNA modification at the lipid headgroup is disclosed. This G-rich oligonucleotide stabilizes micelles in the presence of serum proteins through the formation of a G-quadruplex structure. By extending the RNA sequence at the 3' end, micelle destabilization can be programmed by introduction of a complementary oligonucleotide. Micelle stability can further be tuned by titration of this oligonucleotide, showing that these particles can be programmed to release cargo, whether it be, for example, a hydrophobic drug or an imaging dye.

REFERENCES (1) Li, Y.; Xiao, K.; Luo, J.; Xiao, W.; Lee, J. S.; Gonik, A. M.; Kato, J.; Dong, T. A.; Lam, K. S. Biomaterials 2011, 32, 6633.
(2) Joralemon, M. J.; O'Reilly, R. K.; Hawker, C. J.; Wooley, K. L. J Am Chem Soc 2005, 127, 16892.
(3) Sun, X.; Rossin, R.; Turner, J. L.; Becker, M. L.; Joralemon, M. J.; Welch, M. J.; Wooley, K. L. Biomacromolecules 2005, 6, 2541.
(4) Dong, H.; Dube, N.; Shu, J. Y.; Seo, J. W.; Mahakian, L. M.; Ferrara, K. W.; Xu, T. ACS Nano 2012, 6, 5320.
(5) Dong, H.; Shu, J. Y.; Dube, N.; Ma, Y.; Tirrell, M. V.; Downing, K. H.; Xu, T. J Am Chem Soc 2012, 134, 11807.
(6) Raouane, M.; Desmaele, D.; Urbinati, G.; Massaad-Massade, L.; Couvreur, P. Bioconjug Chem 2012, 23, 1091.
(7) Edwardson, T. G.; Carneiro, K. M.; McLaughlin, C. K.; Serpell, C. J.; Sleiman, H. F. Nat Chem 2013, 5, 868.
(8) Cheong, C.; Moore, P. B. Biochemistry 1992, 31, 8406.
(9) Petraccone, L.; Erra, E.; Randazzo, A.; Giancola, C. Biopolymers 2006, 83, 584.
(10) Arleth, L.; Ashok, B.; Onyuksel, H.; Thiyagarajan, P.; Jacob, J.; Hjelm, R. P. Langmuir 2005, 21, 3279.
(11) Kastantin, M.; Missirlis, D.; Black, M.; Ananthanarayanan, B.; Peters, D.; Tirrell, M. J Phys Chem B 2010, 114, 12632.
(12) Liu, H.; Zhu, Z.; Kang, H.; Wu, Y.; Sefan, K.; Tan, W. Chemistry 2010, 16, 3791.

What is claimed is:

1. A process for synthesizing a stabilized lipid micelle comprising lipid-oligonucleotide conjugate molecules, the process comprising contacting at least one lipid-oligonucleotide conjugate molecule with at least one other lipid-oligonucleotide conjugate molecule,
   wherein the at least one lipid-oligonucleotide conjugate molecule serves as a lipid head-group and associates with the at least one other lipid-oligonucleotide conjugate molecule forming a G-quadruplex through intermolecular bonds that are disrupted by the addition of an antisense molecule complementary to the G-quadruplex,
   wherein the lipid of the lipid-oligonucleotide conjugate molecule comprises 1,2-dioctadecyl-sn-glycerol, cholesterol, or cholic acid,
   wherein the oligonucleotide is 2 to 60 nucleotides in length,
   wherein disruption of the intermolecular bonds disrupts the micelle, and
   wherein the lipid micelle is stable in serum for at least 12 hours.

2. The process of claim 1, wherein the oligonucleotide of the lipid-oligonucleotide conjugate is an oligoribonucleotide.

3. The process of claim 1, wherein the oligonucleotide comprises one or more 2'OMe-, 2'F-, 2'NH3-, or 2'H-modified residue and/or phosphorothioate.

4. The process of claim 1, wherein all the residues of the oligonucleotide are 2' OMe-, 2'F-, 2'NH$_3$-, or 2'H-modified residues or comprise phosphorothioate.

5. The process of claim 1, wherein the oligonucleotide is attached at its 5' end to a lipid molecule of the lipid-oligonucleotide conjugate molecule.

6. The process of claim 1, wherein the micelle further comprises an additional oligonucleotide, at least a portion of which is on an external surface of the micelle, and which portion binds to a receptor protein.

7. The process of claim 6, wherein the receptor protein is present on a cell of a subject.

8. The process of claim 7, wherein the receptor protein is present on a tumor cell of a subject.

9. The process of claim 8, wherein the receptor protein is preferentially expressed on tumor cells over non-tumorous cells of a subject.

10. The process of claim 1, wherein the sequence of a first portion of the oligonucleotide is UGGGU.

11. The process of claim 1, wherein the lipid-oligonucleotide conjugate molecule comprises 1,2-dioctadecyl-sn-glycerol phosphoramidite.

12. The process of claim 1, wherein the diameter of the lipid micelle is 5 to 60 nm.

13. The process of claim 1, wherein the process further comprises contacting the lipid micelle with an amount of a predetermined drug molecule, or of a predetermined imaging molecule, sufficient for uptake of at least a portion of the predetermined drug molecule or imaging molecule into the lipid micelle.

14. The process of claim 13, wherein the predetermined drug molecule is an anti-tumor drug.

15. The process of claim 1, wherein the lipid micelle is stable in serum for at least 24 hours.

16. The process of claim 1, wherein the oligonucleotide is attached at its 3' end to a lipid molecule of the lipid-oligonucleotide conjugate molecule.

* * * * *